US00PP17637P3

(12) United States Plant Patent
Huidobro

(10) Patent No.: US PP17,637 P3
(45) Date of Patent: Apr. 24, 2007

(54) PLUM TREE NAMED 'CONSTANZA'

(50) Latin Name: *Prunus salicina*
Varietal Denomination: Constanza

(76) Inventor: Jose Domingo Godoy Huidobro, Santa Blanca 1296 Lo Barnechea, Santiago (CL)

( * ) Notice: Subject to any disclaimer, the term of this patent is extended or adjusted under 35 U.S.C. 154(b) by 39 days.

(21) Appl. No.: 11/202,796

(22) Filed: Aug. 11, 2005

(65) Prior Publication Data

US 2007/0039081 P1 Feb. 15, 2007

(51) Int. Cl.
*A01H 5/00* (2006.01)

(52) U.S. Cl. ..... Plt./184
(58) Field of Classification Search ..... Plt./184
See application file for complete search history.

(56) References Cited

FOREIGN PATENT DOCUMENTS

CL 38/03 11/2003

OTHER PUBLICATIONS

Upov–rom GTITM Plant Variety Database, 2006/01, GTI Jouve Retrieval Software, Citation for *Prunus* 'Constanza' one page.*

* cited by examiner

*Primary Examiner*—Kent Bell
*Assistant Examiner*—June Hwu
(74) *Attorney, Agent, or Firm*—Wells St. John P.S.

(57) ABSTRACT

A new and distinct variety of plum tree "*Prunus salicina*" and which has been denominated as "Constanza," and which further produces an attractively colored plum which is mature for harvesting and shipment about March 20$^{th}$ to April 10$^{th}$ under the ecological conditions prevailing in the Maipo Valley, near Santiago, Chile.

4 Drawing Sheets

BACKGROUND OF THE NEW VARIETY

The present invention relates to a new, novel, and distinct variety of plum tree '*Prunus salicina*' and which has been denominated varietally as 'Constanza' and more specifically to a plum tree which produces what are considered to be exceptionally high quality, black plums which are mature for harvesting, and shipping about March 20 to April 10 under the ecological conditions existing in the Maipo Valley of Santiago, Chile.

ORIGIN AND ASEXUAL REPRODUCTION OF THE NEW VARIETY

The seedling 'Constanza' was originated by me in 1990, and selected from among a population of seedlings which were derived from a cross-pollination conducted between the 'Larry Anne' plum tree, unpatented, which was the pollen parent; and 'Angeleno' plum tree, U.S. Plant Pat. No. 2,747, and which was used as the seed parent. The resulting seeds from this cross-pollination were then planted in the applicant's breeding beds during the winter of 1991. The seedlings which resulted from this group of seeds were then transplanted to the experimental orchard of the inventor which is located in Nos, San Bernardo in the Maipo Valley of the Chilean Metropolitan region. The plants were then studied and observed during subsequent years. The present variety was selected from among the seedlings then growing in the orchard of the inventor. The variety was selected based upon its vigor, fruit production and quality of fruit. Once identified, the new variety was asexually reproduced and grafted onto Marianna 2624 rootstock (unpatented) for subsequent evaluation in Nos, San Bernardo in the Maipo Valley of the Chilean Metropolitan region. The fruit and the trees produced from this subsequent asexual reproduction were then evaluated for their botanical, and post-harvest behavior for the next 5 years. It has subsequently been determined that these asexual reproductions run true to the original tree. The present tree is the subject of Chilean Plant Variety Rights Certificate 38/03, and which issued on Nov. 12, 2003. Further, the new variety has not been sold, or made publicly available anywhere in the world prior to the effective filing date of the present application.

SUMMARY OF THE NEW VARIETY

The 'Constanza' plum tree is characterized as to novelty, and is noteworthy by producing fruit which have what is considered to be a black skin coloration, and which ripen in the late season of maturity, and approximately 30 days after 'Angeleno' plum tree, and approximately 60 days after the 'Larry Anne' plum tree (unpatented), that is, approximately 20 March to about 10 April under the ecological conditions existing in the Maipo Valley of the Chilean Metropolitan Region. The fruit produced by the present variety is considered to be exceptionally sweet, and has a 16° brix with 6–7 pounds of flesh pressure. In comparison the 'Angeleno' plum tree produces fruit which has a 13° brix with about 5 pounds of flesh pressure, and the 'Larry Anne' plum tree produces fruit having a 14° brix and about 5 pounds of flesh pressure. Other varieties of plums typically have a median of approximately 10° brix. In addition to the foregoing, the fruit produced by the 'Constanza' plum tree is considered to be very large in comparison to that produced by the 'Angeleno' plum tree. Additionally, the skin color of the fruit produced by the 'Constanza' plum tree is darker than the fruit produced by both the 'Larry Anne' and 'Angeleno' plum trees. Moreover, the fruit of the 'Constanza' plum tree has more skin lenticels than both its parents. The fruit of the 'Constanza' plum tree further has a higher level of bloom in relative comparison to the fruit of the 'Larry Anne' and 'Angeleno' plum trees. In relative comparison to its parents, the new variety also produces low amounts of ethylene and has a significant blush. Moreover, the present variety has noteworthy storage and shipping qualities inasmuch as the fruit of the present variety has been kept in cold storage from 75 to 90 days with no deleterious effects noted. In comparison, the fruit produced by the 'Larry Anne' plum tree typically can only be retained in storage for approximately 40 days; and the fruit produced by the 'Angeleno' plum tree can typically be only kept in storage for about 60 days.

BRIEF DESCRIPTION OF THE DRAWINGS

The colors in the enclosed photographs, which are provided, are as nearly true as is reasonably possible in color representations of this type. Due to chemical developments, processing and printing, the leaves and fruit depicted in these photographs may or may not be accurate when compared with the actual specimens. For this reason, future color reference should be made to the color plates (Royal Horticulture Society) and other descriptions provided for hereinafter.

DETAILED DESCRIPTION

Figure 1:
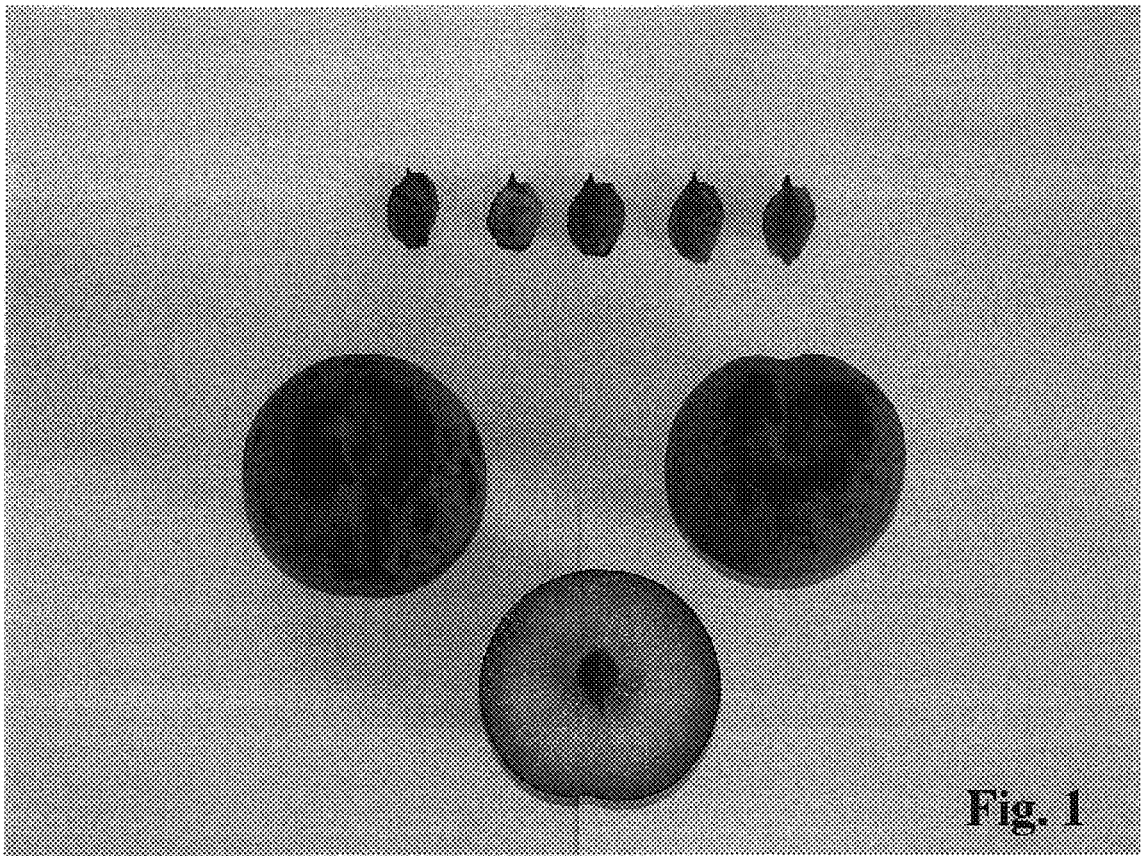
FIG. 1 is a depiction of two whole mature fruit, and one fruit dissected substantially along the equatorial plane to expose the flesh and the pit thereof. Still further, several pits from the fruit of the present variety are shown in that view.
Figure 2:
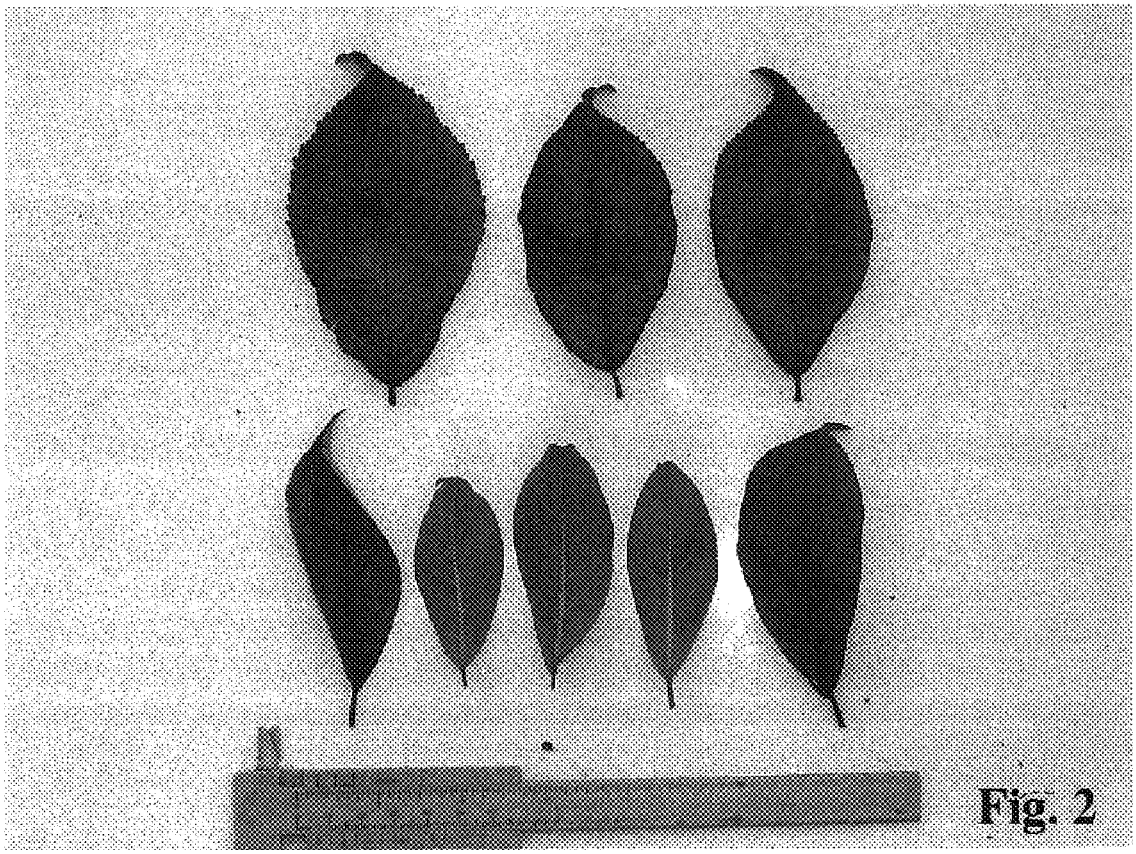
FIG. 2 shows both the dorsal and ventral coloration of typical leaves produced by the present variety.
Figure 3:
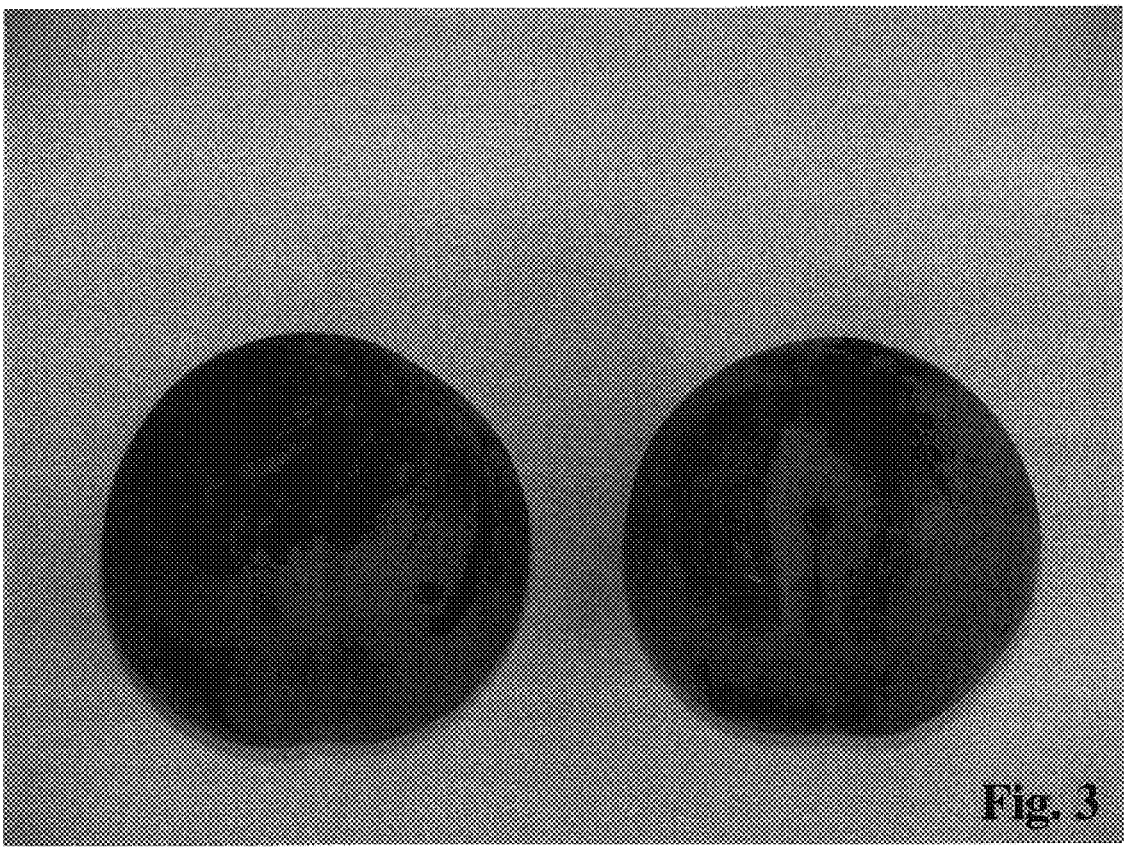
FIG. 3 depicts two whole fruit of the present variety taken from opposite positions.
Figure 4:
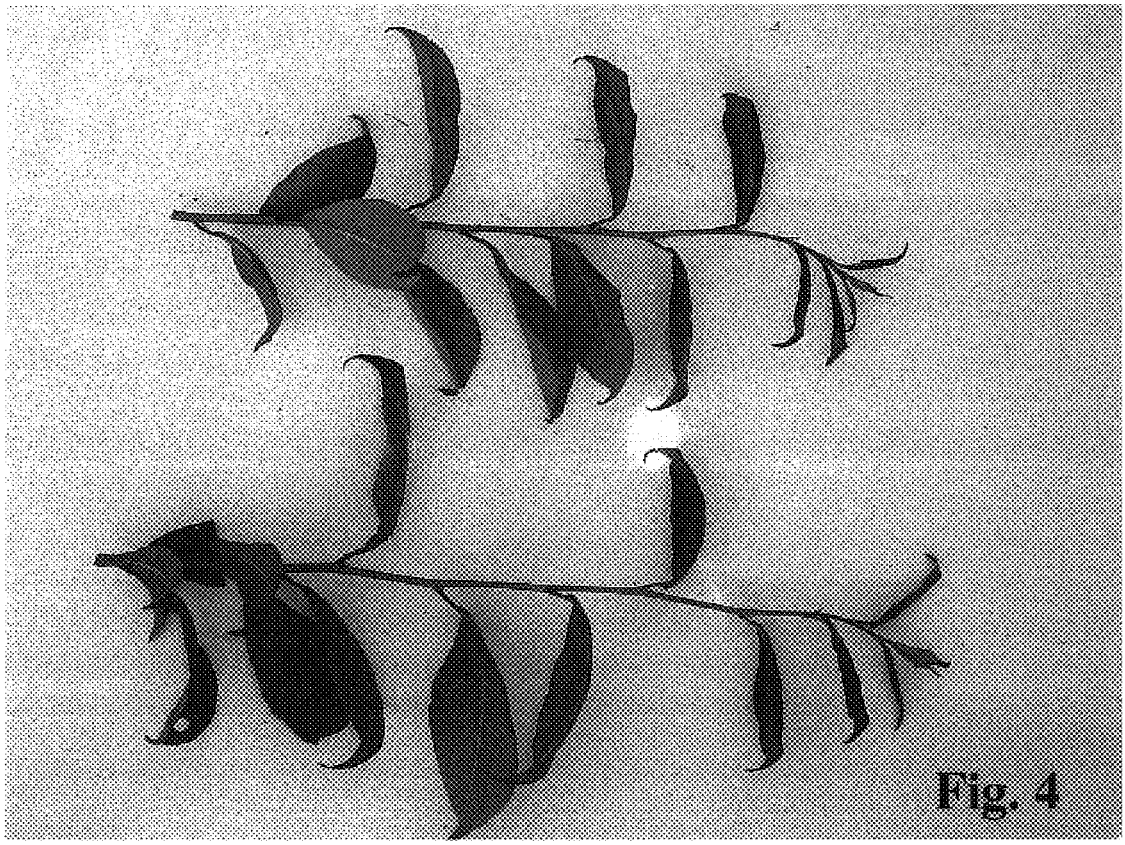
FIG. 4 shows characteristic twigs bearing typical leaves.

Referring more specifically to the pomological details of this new and distinct variety of plum tree, the following has been observed under the ecological conditions prevailing in the inventor's orchard which is located in the Maipo Valley of the Metropolitan Region of central Chile. All major color code designations are by reference to The R.H.S. Colour Chart (Edition 1995) and which is provided by The Royal Horticultural Society of Great Britain.

Tree:

*Size.*—Generally — Medium, as compared to other plum trees varieties having a late date of maturity. The tree of the present variety was pruned to a height of approximately 320 cm. to about 340 cm. at commercial maturity. The presently observed trees are on average 3 years old.

*Productivity.*—Considered very productive. The number of the fruit set varies with climatic conditions, and cultural practices employed during the blooming period and is typically considered not distinctive of the variety. However, trees 6 years and older have produced fruit which have an average weight of about 120 to 140 grams each.

*Vigor.*—Vigorous in comparison with other common plum tree varieties. The present variety, when grafted onto Nemaguard rootstock (unpatented), has grown more than 300 cm during the first growing season. Still further, other plants grafted onto Marianna 2624 rootstock (unpatented) have grown from 200 to about 250 cm. during the first growing season. It has been observed that adult trees typically grow approximately 150 to 200 cm. in height during the growing season.

*Height.*—Generally — Adult trees having an age of about 4–5 years generally attain a height of about 3.5 to 5 meters. The trees are considered very erect and have a noteworthy apical dominance.

*Crown width.*—Typically, adult trees of an age of 4–5 years attain a crown width of about 1.5 to about 2.5 meters.

*Figure.*—Considered very erect and having a distinctive apical dominance.

Trunk:

*Size.*—Considered average.

*Diameter.*—Approximately 14 cm. when measured at a distance of approximately 30 cm. above the soil level. These measurements have been taken from trees that have been previously grafted on to Marianna 2624 rootstock. The measurements were taken at the end of the fourth growth season.

*Bark texture.*—Considered moderately rough, but not distinctive of the variety.

*Bark color.*—Grey-Green (RHS 197C).

*Lenticels.*—Numerous flat, oval lenticels are present. The lenticels range in size from approximately 6 mm. to about 10 mm. in length; and about 1 mm. to about 3 mm. in width. The lenticels have a Grey-Orange color (RHS 166D).

Branches:

*Size.*—Considered to be average as compared to other common plum tree varieties.

*Diameter.*—Four Year Old Trees — About 70 mm. to about 80 mm. when measured at a distance of about 110 cm. above the soil level.

*Diameter.*—Current Season Shoots — About 5 mm. to about 6 mm.

*Internode length.*—One Year Old Shoots — Approximately 8 to 12 mm.

*Internode length.*—Current Season Shoots — Approximately 2 to 5 cm. when measured on trees which are four years old. This internode length is somewhat longer (3 cm. to 5 cm.) on one year old shoots.

*Surface texture.*—Considered moderately rough.

*Crotch angle.*—The present variety of plum tree has a very erect growing habit. Typically, primary branches have a crotch angle of about 70 to about 75 degrees when measured from the horizontal axis. This characteristic is not considered distinct of the variety, however.

*Lenticels.*—Primary Branches. — Numerous flat, oval lenticels are present. The lenticels range in size from about 6 mm. to about 10 mm. in length; and about 1 mm. to about 3 mm. in width. The lenticel color on the primary branches is Grey-Orange (RHS 165C).

*Lenticels.*—One Year Old Shoots — Typically, lenticels are less evident on one year old shoots as compared to the primary branches. These lenticels are about 3 mm. in length; and about 1 mm. in width.

*Bark coloration.*—Primary Branches — Grey-Green (RHS 197C).

*Color.*—Current Season Shoots — Yellow-Green (RHS 144A). This color may vary by the end of the growing season and may be characterized as Grey-Orange (RHS 174A).

*Color.*—One Year Old Shoots — Grey-Brown (RHS 199A).

Leaves:

*Size.*—Considered average for the variety.

*Leaf width.*—On average, approximately 32 mm. to about 36 mm.

*Leaf length.*—On average, about 76 mm. to about 80 mm.

*Form.*—Considered elliptical; Leaf Tip — Shape — Acuminate; Leaf Base — Shape — Attenuated; Base Angle — Less than 90 degrees.

*Marginal form.*—Considered crenate.

*Petiole.*—Length — About 8 mm. to about 10 mm.

*Petiole.*—Width — About 1 mm. to about 2 mm.

*Petiole color.*—Yellow-Green (RHS 148C).

*Color.*—Dorsal surface — Considered a medium green (RHS 137B).

*Color.*—Ventral surface — Yellow-Green (RHS 147B).

*Mid-vein color.*—Yellow-Green (RHS 148C).

*Glands.*—Numbers — Considered few, and positioned on the base of the blade and on the petiole.

Flowers:

*Flower buds.*—Size — Approximately 2 mm. to about 2.5 mm. in length; and about 1 mm. in width.

*Flower buds.*—Surface Texture — Glabrous.

*Flower buds.*—Form — Generally considered conic.

*Flower buds.*—Color — Grey-Orange (RHS 176A).

*Flowers.*—Size — Considered average for the variety. The flowers have an average diameter of approximately 17 mm. to about 20 mm.

*Aroma.*—Considered non-aromatic.

*Flowers.*—Form — The flowers have petals which overlap and touch.

*Stigma.*—Position — Same level as compared with the anthers; Stamens — Numbers — 30–33; Stamens — Length — about 4.5 mm; Filament Color — Green (RHS 135C); Pistil Number — 1; Pistil Length — about 8.5 mm; Styles — Color — Yellow-Green (RHS 154D).

*Blooming period.*—On average, about August 16$^{th}$ to August 23$^{rd}$ under typical Chilean environmental conditions.

*Petal.*—Form — Circular.

*Flower color.*— Considered White (RHS 155A).

*Petal size.*—Considered average, and having a length of about 9 mm.; and a width of about 7 mm.

*Petals.*—Marginal Form — Weekly undulate; Sepal Size — Average, and having a length of about 4.5 mm and a width of 2.7 mm; Petals — Number — 5; Sepal Color — Yellow Green (RHS 144B).

*Pollen production.*—Present. Pollen Color — Yellow (RHS 13B).

Fruit:

*Maturity when described.*—Firm ripe for commercial harvesting and shipment approximately March 20$^{th}$ to about April 10$^{th}$ under typical Chilean environmental conditions. Typically, the earliest first pick begins on 20–25 March under the ecological conditions prevailing in the Maipo Valley of the Chilean Metropolitan Region.

*Size.*—Considered large in comparison to other common varieties.

*Average cheek diameter.*—Approximately 66 mm. to about 70 mm.

*Average axial diameter.*—About 60 mm. to about 62 mm.

*Average fruit weight.*—Typically about 120 grams to about 140 grams when the fruit has a pulp pressure of about 5 pounds to about 7 pounds. This average weight is dependent upon the ambient environmental conditions, and cultural practices, and is therefore not considered distinctive of this particular variety.

*Fruit form.*—Considered rounded and somewhat flattened.

*Symmetry.*—Considered slightly asymmetrical.

*Apex.*—Shape — Considered flat.

*Stem cavity.*—Size — Considered average.

*Stem cavity.*—Width — Approximately 10 mm. to about 12 mm.

*Stem cavity.*—Depth — Approximately 7 mm. to about 8 mm.

*Stem cavity.*—Length — Approximately 12 mm. to about 14 mm.

*Flesh color.*—Variable, but considered Yellow-Green (RHS 1C). This color may vary such that an increasingly yellow color appears in the region around the stone, and the Yellow-Green color appears near the skin as seen in FIG. 1.

*Flesh firmness.*—Considered firm for the variety. The pulp pressure of about 5 pounds to about 7 pounds at commercial maturity appears to have contributed, at least in part, to a post-harvest storage lifetime of about 75 to 90 days.

*Juice production.*—Considered medium juicy.

*Flesh flavor.*—Considered excellent, and very sweet and having a medium level of acidity. Flesh Aroma — Intense and similar to a Japanese plum.

*Brix.*—The present variety has a brix of typically about 16° at commercial maturity.

*Fruit skin.*—Texture — The fruit skin displays a greater number of lenticels than the parent variety Larry Anne.

*Russet.*—Present. The variety displays concentric rings of russet around the stem cavity thereof.

*Fruit blush.*—Abundant. This appears to be an important factor in the post-harvest behavior of the present variety.

*Tendency of crack.*—Not observed.

*Fruit skin color.*—Dark Purple (RHS 187A). This is considered a black plum. Fruit Skin Bloom Intensity — Intense and having a white aspect. This is not distinctive of the variety however. Fruit Skin Flavor — Typical of a Japanese plum.

Stone:

*Type.*—considered semi-clingstone.

*Size.*—Considered small for the variety.

*Stone length.*—Approximately 24 mm. to about 25 mm.

*Stone width.*—Approximately 15 mm. to about 16 mm.

*Stone thickness.*—Approximately 9 mm. to about 10 mm.

*Stone form.*—Generally considered to be elliptical and somewhat rounded in the side and basal views. It should be understood, however, that the stone size may vary depending upon the tree vigor, crop load and the prevailing growing conditions. Therefore the size of the stone is not particularly distinctive of the present variety.

*Stone symmetry.*—Appears symmetrical when viewed ventrally and asymmetrical, when considered in profile.

*Stone.*—Surface — Finely pitted.

*Dorsal groove.*—Shape — Considered broken along the margin.

*Width of ventral zone.*—Considered average for the variety.

*Pistil end.*—Shape — Pointed.

*Shape of the stalk end of the stone.*—Considered narrow.

*Tendency to split.*—Not observed.

*Keeping quality.*—Considered excellent. The present variety has been kept in cold storage conditions for 75 to 90 days with no deleterious effects noted.

*Use.*—The present variety is a plum tree of the late season of maturity, and which has excellent consumer appeal, harvesting and shipping characteristics.

*Pollination.*—The variety has been utilized with other pollinators such as the plum tree variety Larry Anne (unpatented), Wickson (unpatented), and Royal Diamond plum trees (U.S. Plant Pat. No. 6,756).

Although the new variety of plum tree possesses described characteristics when grown under the ecological conditions prevailing in the Maipo Valley of Chile, and which is located in the central zone of the Chilean Metropolitan Region, it should be understood that variations of the usual magnitude and characteristics incident to changes in growing conditions, fertilization, pruning, pest control and horticultural management are to be expected.

Plant/fruit disease susceptibility: Not observed.

Resistance to known plant diseases or pathogens: Not observed.

Having thus described and illustrated in my new variety of plum tree, what I claim is new, and desire to secure by Plant Letters Patent is:

1. A new and distinct variety of plum tree substantially as illustrated and described, and which is characterized principally as to novelty by producing an attractively colored plum which is mature for harvesting and shipment approximately March $20^{th}$ to April $10^{th}$ under the ecological conditions in the Maipo Valley, near Santiago, Chile.

* * * * *